(12) United States Patent
Stubbs

(10) Patent No.: US 11,337,772 B2
(45) Date of Patent: May 24, 2022

(54) IMPLANT FOR TARGETING THERAPEUTIC PROCEDURE

(71) Applicant: HOLOGIC, INC., Marlborough, MA (US)

(72) Inventor: James B. Stubbs, Palo Alto, CA (US)

(73) Assignee: HOLOGIC, INC., Marlborough, MA (US)

( * ) Notice: Subject to any disclaimer, the term of this patent is extended or adjusted under 35 U.S.C. 154(b) by 252 days.

(21) Appl. No.: 15/982,903

(22) Filed: May 17, 2018

(65) Prior Publication Data

US 2019/0110858 A1    Apr. 18, 2019

Related U.S. Application Data

(63) Continuation of application No. 15/466,619, filed on Mar. 22, 2017, now abandoned, which is a
(Continued)

(51) Int. Cl.
*A61B 90/00* (2016.01)
*A61F 2/12* (2006.01)
(Continued)

(52) U.S. Cl.
CPC .............. *A61B 90/39* (2016.02); *A61B 17/22* (2013.01); *A61F 2/12* (2013.01); *A61L 31/044* (2013.01);
(Continued)

(58) Field of Classification Search
CPC .......... A61L 27/18; A61L 27/56; A61L 27/58; A61L 31/044; A61L 31/148; A61B 2090/3908; A61B 90/39; A61B 17/22; A61B 2017/00004; A61B 2090/363; A61B 2090/3925; A61B 2090/3966; A61B 2090/3987; A61B 2090/3995; A61B 8/481; A61F 2/12; A61F 2/0059; A61F 2/0077; A61N 5/1049; A61N 2005/1051; A61N 2005/1089; A61N 2005/1091; A61N 2005/1096; A61N 5/02; A61N 5/1015; A61N 5/1069; A61N 5/107; A61N 5/1077; A61N 7/02; A61N 5/1039; A61N 5/1042; A61N 5/1045; A61N 5/1067; C08L 67/04; A61K 49/006; A61K 49/222; A61M 31/002

See application file for complete search history.

(56) References Cited

U.S. PATENT DOCUMENTS 5,501,706 A * 3/1996 Arenberg ................... A61F 2/18
                                                                 433/201.1
5,545,229 A * 8/1996 Parsons .................... A61F 2/442
                                                                  623/17.15
(Continued)

*Primary Examiner* — Mark D Remaly
(74) *Attorney, Agent, or Firm* — Jones Robb, PLLC

(57) ABSTRACT

An implantable device has a body that is substantially rigid and has a predetermined shape. The body is further bioabsorbable and has a density less than or equal to about 1.03 g/cc. When the device is implanted in a resected cavity in soft tissue, it causes the cavity to conform to the predetermined shape. The implantable device is further imageable due to its density being less than that of soft tissue such that the boundaries of the tissue corresponding to the predetermined shape can be determined.

18 Claims, 4 Drawing Sheets

Related U.S. Application Data continuation of application No. 14/581,807, filed on Dec. 23, 2014, now abandoned, which is a continuation of application No. 12/173,881, filed on Jul. 16, 2008, now abandoned.

(60) Provisional application No. 60/949,963, filed on Jul. 16, 2007.

(51) Int. Cl.
    *A61N 5/10*     (2006.01)
    *A61B 17/22*     (2006.01)
    *A61L 31/04*     (2006.01)
    *A61L 31/14*     (2006.01)
    *A61M 31/00*     (2006.01)
    *A61N 5/02*     (2006.01)
    *A61N 7/02*     (2006.01)
    *A61B 17/00*     (2006.01)

(52) U.S. Cl.
    CPC ......... *A61L 31/148* (2013.01); *A61M 31/002* (2013.01); *A61N 5/02* (2013.01); *A61N 5/1039* (2013.01); *A61N 5/1045* (2013.01); *A61N 5/1049* (2013.01); *A61N 5/1067* (2013.01); *A61N 5/1069* (2013.01); *A61N 5/1077* (2013.01); *A61N 7/02* (2013.01); *A61B 2017/00004* (2013.01); *A61B 2090/363* (2016.02); *A61B 2090/3908* (2016.02); *A61B 2090/3925* (2016.02); *A61B 2090/3966* (2016.02); *A61B 2090/3995* (2016.02); *A61N 5/107* (2013.01); *A61N 5/1042* (2013.01); *A61N 2005/1051* (2013.01); *A61N 2005/1089* (2013.01); *A61N 2005/1091* (2013.01); *A61N 2005/1096* (2013.01)

(56) References Cited

U.S. PATENT DOCUMENTS

| | | | |
|---|---|---|---|
| 6,214,045 B1 * | 4/2001 | Corbitt, Jr. | A61F 2/12 |
| | | | 424/400 |
| 2005/0080338 A1 * | 4/2005 | Sirimanne | A61B 90/39 |
| | | | 600/431 |
| 2005/0101860 A1 * | 5/2005 | Patrick | A61N 5/1015 |
| | | | 600/433 |

* cited by examiner

IMPLANT FOR TARGETING THERAPEUTIC PROCEDURE

RELATED APPLICATIONS

This application is a continuation of U.S. patent application Ser. No. 15/466,619, filed Mar. 22, 2017, which is a continuation of U.S. patent application Ser. No. 14/581,807, filed Dec. 23, 2014, now abandoned, which is a continuation of U.S. patent application Ser. No. 12/173,881, filed Jul. 16, 2008, now abandoned, which claims priority to U.S. Provisional Patent Application No. 60/949,963, filed Jul. 16, 2007, the disclosures of which are incorporated herein by reference in their entirety.

BACKGROUND

Two trends have become significant in driving the delivery of medical treatments: 1) treatments, be they drugs, energy or surgery, are moving towards local and focal delivery, and 2) treatments are being tailored and optimized for each patient based on their specific anatomy, physiology and disease features. These directions both are designed to minimize the likelihood of adverse effects from the therapies as well provide a more patient-specific treatment, which in theory should improve disease cure or control rates.

These trends were started in surgery where large, open surgical procedures have been and continue to be replaced by minimally-invasive procedures and endoscopic procedures. Drug therapies are moving to more local delivery, directly to the treatment site (e.g., drug eluting stents and Gliadel wafers for brain tumors). Until recently, the desire to do the same in radiation therapy has been hampered by inadequate technology for focused delivery. However, significant progress in local radiation delivery has been accomplished in the brachytherapy subspecialty of radiation oncology, most notably in prostate and breast cancer patients. Breast brachytherapy, whereby the radiation source is inserted temporarily into an implanted catheter inside the breast has had great success in popularizing both accelerated and smaller volume treatments. These trends have been less successful at improving the delivery of external beam radiation.

External beam radiation therapy (EBRT) is one of the most common adjuvant therapies for cancer patients in the U.S., with chemotherapy being the other one. EBRT is delivered to cancer patients as either the first line of therapy (for non-resected cancers) or as a means of maximizing local control of the cancer following surgical removal of the tumor. In EBRT, one or more beams of high energy x-rays are aimed at the part of the body needing radiotherapy. A linear accelerator (often called a linac) produces the beams and has a collimator that helps to shape the beams as they exit the linac. It is very common for a tumor to be treated using two or more beams, each of which is delivered from different directions around the tumor, and that all intersect at the tumor site. In this manner, the tissue surrounding the target can be exposed to lower radiation doses than the sum of the treatment beams yields at the tumor target. The tumor target volume is delineated by the radiation oncologist using CT scans of the patient. The tumor target volume and radiation dose prescription parameters are entered into a treatment planning computer. Treatment planning software (TPS) then produces a plan showing how many beams are needed to achieve the radiation oncologist's prescription dose, as well as the size and shape of each beam.

The complete course of EBRT is divided (called fractionation) into numerous small, discrete treatments called fractions. A typical prescribed dose of 60 Gray (Gy) is fractionated into 30 daily treatments of 2 Gy per day. During a fraction, the treatment beam may be "on" for ~1 minute. Thus, the full radiotherapy treatment takes about 6 weeks (5 fractions per week) to complete.

Historically, EBRT has been practiced exactly as has chemotherapy, namely, the radiation doses delivered to the patient are limited only by the tolerance of normal tissues surrounding the site to be treated. Hence, often, the radiation therapy is continued until side-effects become intolerable for the patient. Effectively, radiation therapy has been a "radiate until the patient can't take it anymore" type of treatment. The target volume, in which it is desired to deliver essentially 100% of the prescribed radiation dose, has historically been defined as the tumor (the gross tumor volume, or GTV) plus a surrounding volume of tissue that is like to harbor microscopic tumor cell foci (the clinical target volume, or CTV). Another margin of surrounding normal tissue is added to the CTV to account for errors in positioning of the patient for therapy and movement of the tumor site both during a fraction and between fractions. Chest and upper abdomen radiation therapy (e.g., lung cancer and pancreatic cancer) are two examples where large margins are needed to make sure the changes in tissue position during respiration do not result in the target leaving the beam during some portion of the fraction.

In the last few years, the treatment planning software and linear accelerator technology have dramatically improved in their ability shape the radiation therapy beams to better avoid nearby sensitive structures. The latest treatment planning software allows the radiation oncologist and medical physicist to define the volume of tissue to be treated using CT scans and provide therapy constraints (e.g., minimum radiation dose inside the target volume, maximum radiation dose to structures nearby target volume) and have the software compute the beam angles and shapes in a process called inverse treatment planning. Improved beam shaping is achieved using a technique called Intensity Modulated Radiation Therapy (IMRT). Another feature of the newer linacs is a type of radiographic (and/or ultrasonic) imaging that is used to better position the patient and his/her tumor for more accurate targeting of the treatment beams. This latter method is called Image Guided Radiation Therapy, or IGRT.

Both IMRT and IGRT techniques use numerous, smaller and better focused beams that intersect at the target volume. IGRT differs from IMRT in at least one important aspect—imaging prior to each fraction is used to reduce positioning errors and make sure the treatment beam is properly targeted. Typically, IGRT uses bony anatomy (e.g., pelvic bones for prostate patients) for radiographic targeting and soft tissue interfaces (prostatic capsule and bladder wall) for ultrasound targeting. Rarely, implanted radio-opaque markers (e.g., Visi-Coil) have been used to facilitate targeting for IGRT. Radio-opaque markers are very common for delineating the target for post-lumpectomy radiation therapy treatment planning, however these markers have not been used for targeting each fraction or each beam of every fraction as is done in IGRT.

IMRT uses a special type of collimator, a multi-leaf collimator (MLC) that changes the shape of the beam during each fraction to modulate or "sculpt" the radiation dose to more closely fit the actual target volume shape in three dimensions. Linacs with MLCs can control the size and shape of the beam to within a few millimeters accuracy.

IGRT is a relatively new option on linacs. New linacs are being sold today that have on-board imaging capability via mega-voltage (MV) or kilo-voltage (KV) x-rays/fluoroscopy. The on-board imaging capability can also be retrofitted to existing linacs. On-board imaging is a technical capability that has been introduced into the newest linac product lines by all the major linac manufacturers (Varian Medical Systems, Elekta, Tomotherapy, Accuray and Siemens). While the technology made by these companies provides the possibility of performing better targeting for external beam radiation therapy, the targets (e.g., bony anatomy) is inadequate for accurate targeting.

As described above, targeting the external beam radiation therapy accurately requires one to point out the target using fiducial markers having different radiographic properties than that of surrounding tissue (e.g., bone, and soft tissue). To date, this has been accomplished using radio-opaque markers (e.g., permanently implanted foreign bodies). Alternatively, Patrick and Stubbs described a device and method for shaping and targeting EBRT using a temporarily implanted balloon catheter (published United States patent application US 2005/0101860 A1). This device and method required implantation of a foreign body whose removal necessitated a second surgical procedure. Removal of this foreign body would leave a volumetric defect in the patient's breast.

Hence, the need exists for a better device and method for positioning the target volume and providing a visual target for the external beam treatments, without introduction of foreign bodies requiring surgical removal at a later date and without leaving behind a surgical defect that adversely affects cosmetic results.

SUMMARY

The present invention includes methods, as well as devices and systems, for the delivery of therapeutic rays to regions of tissue within a patient, or for improving the accuracy and precision of such methods, devices and systems. In a first aspect, the invention includes a method for treating a proliferative tissue disease in a patient. The method includes excising diseased tissue from the patient and thereby creating a tissue cavity. A bioabsorbable implant is then placed within the tissue cavity. The implant can have a predetermined shape and include a means for visualizing the implant. The location of the implant within the patient is then determined and tissue surrounding the tissue cavity is treated with therapeutic rays.

In a further aspect of the invention, a method for targeting and delivering therapeutic rays to a patient's soft tissue is provided. This method includes imaging an implanted device within soft tissue in the patient where the implanted device is substantially rigid, has a predetermined shape, and has a density that is lower than the density of the patient's soft tissue. A region of target tissue surrounding the implanted device is then determined, a radiation dose from a source external to the patient is targeted to the target tissue, and the targeted radiation dose is delivered.

In a still further aspect of the invention, a system for targeting therapeutic rays to target tissue surrounding a tumor resection cavity is provided. The system includes an implantable device having a body that is substantially rigid and has a predetermined shape. The body is further bioabsorbable and has a density less than or equal to about 1.03 g/cc. When the device is implanted in a resected cavity in soft tissue, it causes the cavity to conform to the predetermined shape. The implantable device is further imageable due to its density being less than that of soft tissue such that the boundaries of the tissue corresponding to the predetermined shape can be determined.

BRIEF DESCRIPTION OF THE DRAWINGS

The invention will be more fully understood from the following detailed description taken in conjunction with the accompanying drawings.

DETAILED DESCRIPTION

The invention described herein use implantable devices that can allow for more accurate targeting of external beam radiation to the region of tissue that is to be treated. The devices provide a reproducibly-shaped 3-dimensional target that is used to focus the radiation therapy treatment beams directly onto the targeted tissue—for example, the tissue surrounding a resected tumor cavity. The device can be formed of an absorbable material that is implanted at the time of tumor resection and requires no second procedure to remove (it dissolves in situ leaving no foreign material in the patient's body).

Figure 1:
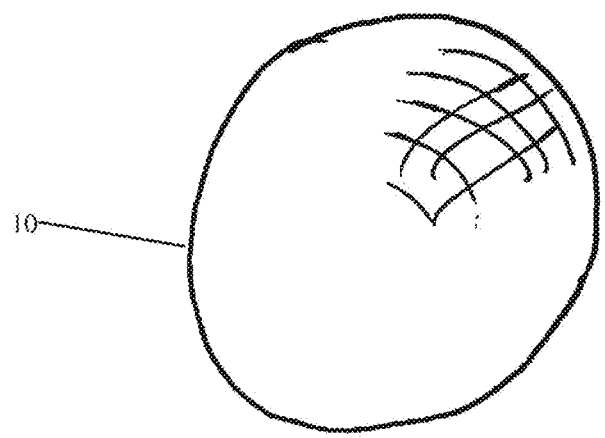
FIG. 1 illustrates an implantable device of the invention.

In one embodiment, the invention includes a bioabsorbable surgical implant 10 (illustrated in FIG. 1 in a spherical configuration) with at least one integral radiographic (or ultrasonic) visualization (targeting) property. The device can have sizes ranging from 5 mm in diameter to 5 cm in diameter (other sizes are possible depending upon the application). Preferably, the implant 10 has a predetermined shape that can facilitate easy and simple treatment beam profiles, such as spheres, ellipsoids, parallelopipeds (e.g., rectangular boxes). In this way, the implant can be visualized, and its contours (and thus the contours of the target tissue to be treated—typically marginal regions surrounding an excised tumor) readily determinable. Treatment can then be applied to the target tissue. The size and shape of the implant can be varied to correspond to the most common resection cavity sizes and shapes. The implant may be in its predetermined shape before implant or assume that shape upon mechanical manipulation or implantation (e.g., it may be evacuated such that upon contact with air or fluids it absorbs the air or fluids and returns to its intended shape).

The implant 10 can have one or more of the following key features:

1) Integrated targeting feature (altered material composition allowing radiographic or ultrasonic localization);

2) Multiple sizes of implant, each having a relatively fixed shape upon implantation;

3) Bioabsorption over a specified or desired time period;

4) Sufficient volume to replace resected tissue preventing poor cosmetic outcomes by eliminating volume defects due to tissue loss (breast models); and 5) The device/implant can be inserted at the time of surgical resection of the tumor or as a minimally invasive procedure at some time period following surgery.

Figure 2:
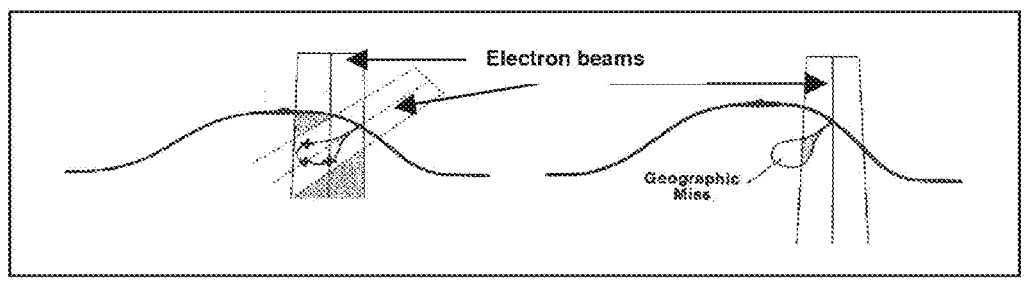
FIG. 2 illustrates the targeting and delivery of therapeutic rays as it is known in the prior art.

It is important that the implanted targeting device 10 be visible on radiographic films (MV and/or KV x-rays) and ultrasound equipment. FIG. 2 illustrates how this is important. On the left, two electron beams are properly targeted onto a lumpectomy cavity and its margin. On the right a single electron beam, using only the skin scar as its target, misses much of the cavity and its margin. The figure on the left is the result of being able to see the target for every fraction and adjust the beam to make certain the target is hit. The figure on the right is the result of using movable or deformable anatomical landmarks for the target.

While a number of methods, devices, and materials are known to provide radiographic marking, in a preferred embodiment, the implant 10 can have "negative contrast" (a density less than that of soft tissue), which provides radiographic and ultrasonic contrast to facilitate visualization on these imaging modalities. Ultrasound visualization may also be accomplished when the material of the device has different echogenic properties as to those of tissue surrounding it. Other properties may be beneficial for these and other imaging modalities. With the requisite physical properties that allow on-board imaging systems to "see" the target provides the means to reposition the patient and alter the treatment beams to insure optimal targeting. This targeting can be used for every fraction delivered to the patient.

Preferably, the implant 10 is completely bioabsorbable, though other configurations with at least portions of the implant being non-resorbable may be desirable. One example is the incorporation of one or more wireless transponders that provide wireless signals that can be interpreted as to the 3-D location (in the Linac's frame of reference) of the transponders. Calypso Medical's Beacon Transponder™ is an implantable transponder that provides localization data for targeting purposes (it is not, however, an image guided localization device). There are numerous ways to alter bioabsorbable materials to achieve the desired imaging capability. One way is to incorporate air or gas pockets or bubbles into the resorbable material.

Various materials that could be used to construct such an implant include known biosorbable materials such as polyglycolic acid (Dexon, Davis & Geck); polyglactin material (Vicryl, Ethicon); poliglecaprone (Monocryl, Ethicon); and synthetic absorbable lactomer 9-1 (Polysorb, United States Surgical Corporation). Other materials include moldable bisorbable materials such as PLLA and PLLA/PGA blends. Other foamable materials that can be utilized in the present invention include, without limitation, proteins such as collagen, fibronectin, laminin and fibrin, most preferably collagen, and high molecular weight polysaccharides, such as heparan sulphate, chondroitin sulphate, hylauronic acid and dermatan sulphate. Mixtures of any of the aforementioned materials also can be used, as required. The materials can be modified, by cross-linking for example, to control degradation rates over varying lengths of time, after which they are substantially or completely resorbed.

Collagen is a preferred material. Examples of collagen materials and methods for making them can be found, for example, in U.S. Pat. No. 5,019,087 to Nichols; U.S. Pat. No. 3,157,524 to Artandi; and U.S. Pat. No. 3,520,402 to Nichols et al., each of which is hereby incorporated by reference for its teachings of collagen materials and methods of manufacture.

In one preferred embodiment, the device has multiple layers of bioabsorbable materials. For example, the core of the largely spherical device is filled with collagen (in one of its many physical forms) and is surrounded by a layer of other, stiffer or more resilient bioabsorbable materials such as Vicryl. The Vicryl material can laid down as a sheet of Vicryl or as a winding of Vicryl thread. Alternatively, the outer layer may be a continuous shell or a discontinuous (e.g. geodesic) structure made of molded PLLA or PLLA/PGA blend. This layer of tougher material produces the resiliency of the device to maintain a specific shape (e.g., a sphere) and the internal bioabsorbable material (e.g., collagen) serves as a filler. The outer material may govern the overall rate of resorption and may include a semi-permeable membrane or as a temporarily impermeable membrane.

In one embodiment, the density of the implant 10 should be less than 1.04 gram/cc. It may be substantially lower (<0.80 gram/cc), slightly lower (0.95-1.03 gram/cc) or intermediately lower (0.80-0.95 gram/cc) than the density of soft tissue. There may be utility in an implant with density higher than that of soft tissue as that type material can be easily seen on KV x-rays. The density should not be significantly larger as too much attenuation of the radiation beams may result in dose perturbations that current treatment planning systems cannot compensate for. Thus higher densities should not exceed about 1.3 gram/cc. For these higher contrast embodiments, the higher contrast material does not need to be uniformly spread throughout the device. Rather, a portion of the outer aspect of the device may be high density (contrast) with the inner aspect being of lower density. For example, in a spherical embodiment, the outermost few millimeters of material may be impregnated with x-ray media (e.g., barium sulfate, Iohexol™, Omnipaque™ or other biocompatible high density matter), while inside this shell, the device would be made of any bioabsorbable material of lower density.

The material for implant 10 should be rigid enough to provide a fixed and predetermined shape in situ. A fixed and predetermined shape can be a significant advantage in that it provides a standard shape for targeting. In deformable tissues (i.e., breast and perhaps lung), having the implant remodel the surrounding surgical margins into a specific shape (i.e., a sphere) allows the clinical target volume and planning target volumes (i.e., the target for radiotherapy) to also take this shape. For resected breast cancer cases, the resection cavity has irregular shape, the shape can change day to day and even during different portions of the respiratory cycle, and the cavity can grow or shrink over the time period during which radiation therapy is to be delivered. Having the target volume in the same shape every day of therapy increases the probability of always hitting the target and reduces the chance of a "geographic miss". A simple shape such as a sphere is one of the easiest shapes for linacs to sculpt to, using either the multi-leaf collimator or compensator. Thus, shaping the treatment filed is substantially easier, and quicker to plan and execute. The desired shapes are ones in which the external surface(s) is(are) convex rather than concave.

The sizes of the implant are most preferably in the 2-4 cm diameter range (diameter of the major axis). Other sizes may be preferable, depending on the patient's anatomy and anatomical location of the target. For breast, the diameter range of 2-4 cm is preferred.

The implant should take a rather stiff configuration in vivo. This will allow the implant to better conform the surrounding tissue to its shape. It is also a benefit to have some rigidity (though not rock hard) in that the shape will remain the same for each radiation therapy treatment. It is not necessary, and is in fact less desirable, for the implant to be completely rigid until resorbed. The desirable property is one that is deformable (to improve comfort for the patient) but rebounds to its desired shape upon release from stress or tension. For example, the breast implant may deform to a compressed shape (think of a beach ball being pressed between two hands) when the patient is wearing a bra or is prone, but returns to spherical shape when the bra is removed and the patient is supine. As used herein, the term "substantially rigid" refers to the preferred situation in which the implant reproducibly provides the desired predetermined shape to the tissue surrounding a tumor resection cavity while allowing some compliance for the purpose of providing implantation through a smaller incision and/or to provide increased comfort for the patient.

The most desirable rate of resorption for bioabsorbable implants will depend on the specific application and anatomic location. In all cases, it is desired that the implant maintain its size, shape and imaging capacity until radiation therapy is complete. Those experienced in radiation therapy will realize this spans a wide range of time intervals. For patients who will move swiftly to radiation therapy, and receive a hypofractionated radiation therapy, the resorption can start as early as 3 weeks post implant. For others, the radiation therapy may not start for 12-18 weeks post surgically and may last 7 weeks, thus requiring an implant that remains fully functional for as long as 6 months.

The rate of resorption can be controlled by the manufacturing techniques used to produce the bioabsorbable material. Alternatively, the inner material may be a substance that resorbs fairly quickly when in contact with bodily fluids or tissue, but surrounded by a more slowly resorbing outer shell or matrix that dissolves more slowly (thus governing the rate of the implants absorption). Various configurations and materials are also described in U.S. Pat. No. 6,638,308 to Corbitt Jr. et al, which is hereby incorporated by reference. The rate of bioabsorption may also be dictated by the rate at which tissue in-growth may occur (which fills the surgical defect as the implant resorbs).

Regardless of the rate of resorption, having the implant largely bioabsorb means there is no second surgery to remove foreign material from the patient. The controlled absorption allows the implant to remain in place until radiotherapy is complete, and in the case of breast radiotherapy, to replace the resected tissue until the body's healing response replaces it with fibrous tissue.

The implant can be ideally inserted upon completion of the tumor resection, but prior to closing of the surgical wounds. If done in this fashion, one excellent embodiment of the invention is a preformed bioabsorbable implant having the desired size and shape, without need for the surgeon to alter it in any fashion prior to implant. Alternatively, the implant may be adjustable in terms of size or shape by the surgeon using surgical instruments readily available in most operating rooms (e.g., scissors), or by a special tool supplied with the implant (e.g., hemi-spherical cutting tool that rounds the edges of the implant as it is resized.

Figure 3:
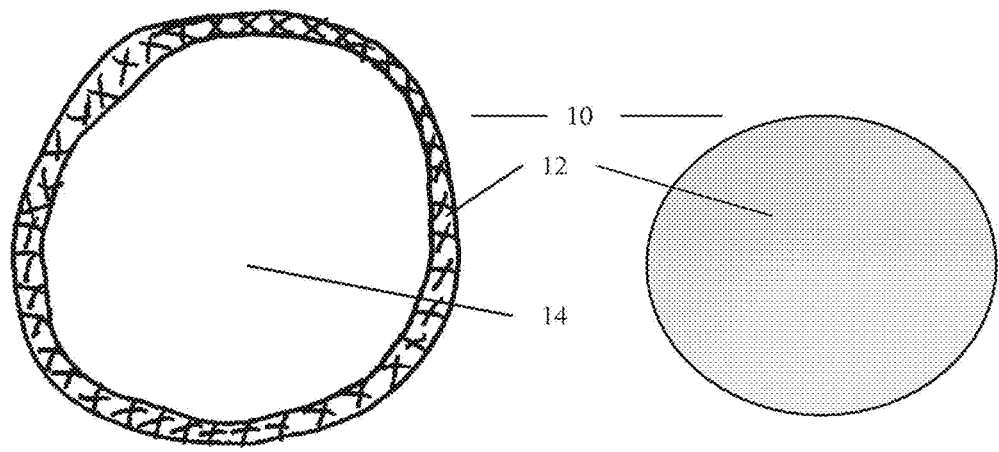
FIG. 3 provides a cross-sectional view of the device of FIG. 1, with a multi-layered version on the left and a single-layered version on the right.

As illustrated in FIG. 3, the implant 10 can be a single layer as illustrated on the right, or the implant 10 can be a multi-component system as illustrated on the left. For the multi-component system, a portion (e.g., the outer shell 12) of the implant is inserted into the resection cavity and the inner bioabsorbable materials 14 infused or injected into the shell, causing it to attain its desired size and shape. One or both of these steps can be performed prior to closing the surgical wounds (open implantation) or both can be performed after closing (immediately post-surgically or after some time has passed following the surgery) using minimally invasive methods (e.g., laparoscopically or under ultrasound guidance). If these steps (or one step) are performed post-surgically, the implant or components of the implant can be inserted into the cavity using a variety of techniques. The preferred method involves using a trocar or cannula to access the cavity and provide a conduit for subsequent insertion of the implant or implant components.

There are a variety of methods of interest to achieve a fully filled implant. The implant shell can be filled remotely using a syringe filled with the inner material. The syringe contents are injected into the implant shell via a long needle or cannula attached to the syringe and piercing the surface of the shell. Instead of a needle, a long flexible tube may be used. Also, a metering can system can be used. In this embodiment, a metering can contains a specific, excess volume of the inner absorbable material. A dial or meter adjustment can be made on the can that will allow the user to dispense a specified volume of inner material without having to further monitor the amount dispensed or how full the implant has become.

Figure 4:
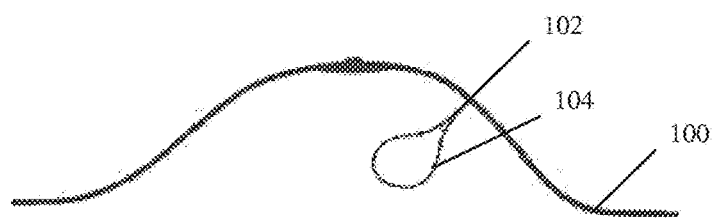
FIG. 4 illustrates a resected tumor cavity in soft tissue as is known in the prior art.

A method according to the invention for treating these and other malignancies begins by surgical resection of a tumor site to remove at least a portion of the cancerous tumor and create a resection cavity as illustrated in FIG. 4. As illustrated, an entry site or incision 102 is created in patient 100 in order to remove tissue and create an irregularly shaped cavity 104.

Figure 5:
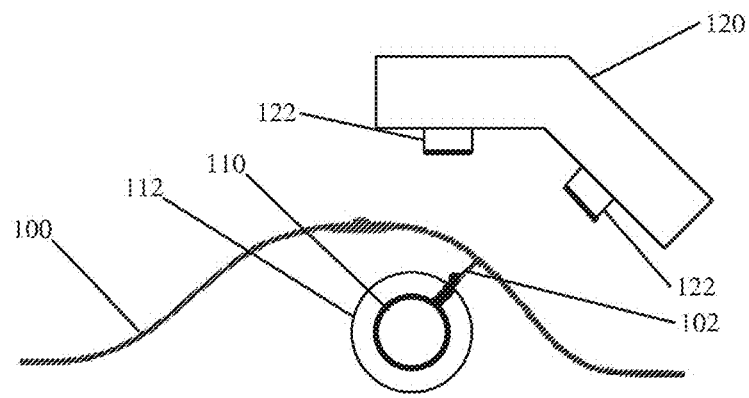
FIG. 5 illustrates the delivery of therapeutic rays according to the invention.

Following tumor resection, as further illustrated in FIG. 5, an implant of the invention 10 is placed into the tumor resection cavity 104. This can occur prior to closing the surgical site 102 such that the surgeon intra-operatively places the device, or alternatively device 10 can be inserted once the patient has sufficiently recovered from the surgery. In the later case, a new incision for introduction of device 10 can be created. In either case, the surface of device 10, which is preferably sized and configured to reproducibly position tissue surrounding the resection cavity 102 in a predetermined geometry, is placed within the resected tissue cavity.

Following insertion of the implant 10, such as by an open method or using a mini-open or minimally invasive procedure, the implant occupies the tissue cavity 102 and supports the surrounding target tissue 112 until such time as it resorbs or biodegrades. Where the implant 10 is sponge-like or porous, after initial implantation the patient's own fluids, fibroblast, and stem cells, such as adipocytes, vascular stem cells, and others, can permeate the implant. In the case of a small implant, such permeation would occur naturally, subsequent to implantation. In the case of a larger implant, providing the implant at least partially filled with fluids prior to implantation may be indicated.

With device 10 in place, it supports the target tissue 112 surrounding the tissue cavity and reduce tissue shifting. In addition, the surface of device 10 can position the target tissue 112 in a predetermined geometry. For example, a spherical implant 10 as illustrated can position the target tissue 112 surrounding the tissue cavity 104 in a generally spherical shape. With the target tissue 112 positioned, a defined surface is provided so that radiation can more accurately be delivered to the previously irregular tissue cavity walls. In addition, device 10 helps reduce error in the treatment procedure introduced by tissue movement. The positioning and stabilization provided by device 10 greatly improves the effectiveness of radiation therapy by facilitating radiation dosing and improving its accuracy. The result is a treatment method which concentrates radiation on target tissue and helps to preserve the surrounding healthy tissue.

Prior to delivering radiation, but after placing the device 10, device 10 and the surrounding target tissue 112 can preferably be visualized with an imaging device, including by way of non-limiting example, x-ray, ultrasound, MRI, CT scan, PET, SPECT and combinations thereof. These imaging devices provide a picture of the device 10 and the surrounding target tissue 112 to assist with the planning of external radiation therapy. To aid with visualization, device 10 can be constructed of materials which highlight its surface during the imaging procedure, for example, the surface may include in its construction a radio opaque material. Thus, the device shapes the cavity to a shape to which it is more easy to conform the radiation therapy beams (as compared to an irregular cavity). The device then provides a target for better repositioning of the patient's targeted tissue before each fraction of treatment. Finally, it can provide a means of real-time tracking the motion of the target volume so that the beams can either move with the target or can be turned on and off as the target moves out of and back into the beams' path.

In a preferred embodiment, the imaging modality takes advantage of the implant 10 having a lower density than the surrounding soft tissue. As explained above, the implant can preferably have a density of less than or equal to about 1.03 g/cc in order for it to be readily imageable. In addition, the imaging modality can rely on the implant having a predetermined shape and size in order to accurately locate the surface of the implant, and thus the surface of the target tissue 112.

In the case of external radiation therapies such as three-dimensional conformal radiation therapy (3DCRT) and IMRT, the imaging procedures provide a map of the residual tissue margin and assist with targeting tissue for radiation dosing. The radiation beams are then adapted for delivering a very precise radiation dose to the target tissue. With device 10 positioning the tissue surrounding the resection cavity, there is less danger of the target tissue shifting (within the body) and thus having the planned radiation missing the PTV and needlessly damaging healthy tissue.

Some treatment regimens require repeated radiation dosing over a course of days or weeks, and device 10 can be used in those cases to repeatedly position the tissue surrounding the resected tissue cavity. These steps can be repeated as necessary over a course of a treatment regimen. Preferably, the implanted device 10 remains in place without intervention, e.g., without removal or actions to change its configuration, throughout the course of treatment.

Another embodiment of the invention incorporates fiducial markers that provide real-time, wireless information about the device's spatial position relative to the origin of a coordinate system in the treatment room (e.g., the isocenter of the radiation delivery device or the radiation beam's source location). The spatial position data can be used to correct errors in target volume location. For example, by adjusting the patient's body position on the treatment couch and/or altering the radiotherapy beams' shape and direction to correct for the altered PTV position. Preferably, the real-time, wireless feedback allows correction of positioning errors prior to delivery of each fraction of radiation. Fiduciary markers can also provide users a more accurate PTV position and thereby allow greater normal tissue sparing and smaller normal tissue margins within the PTV. Preferably, the fiducial markers and their detection systems are radio-opaque markers that are imaged radiographically (e.g., fluoroscopically) or transponders that signal their positions to a receiver system. An exemplary fiducial marker is the Beacon Transponder, made by Calypso Medical Technologies of Seattle, Wash.

Positioning fiducial markers on device 10 provides an advantage over other placements of such markers (e.g. placement within a tumor). For example, by placing a fiducial marker in or on a known location on the device 10 having a predetermined shape, the position of the implant surface can be precisely determined. In addition, a marker positioned on the outside of device 10 can be used to delineate the surrounding target tissue (a.k.a. the PTV). As an additional benefit of having the marker positioned on the device, a separate insertion step is not required for the marker.

In addition to external radiation, other treatments can supplement the method of the present invention. Other treatments can include supplying treatment material to the tissue surrounding the resection cavity, e.g., a chemotherapy drug, or a radiation enhancing material.

Figure 6:
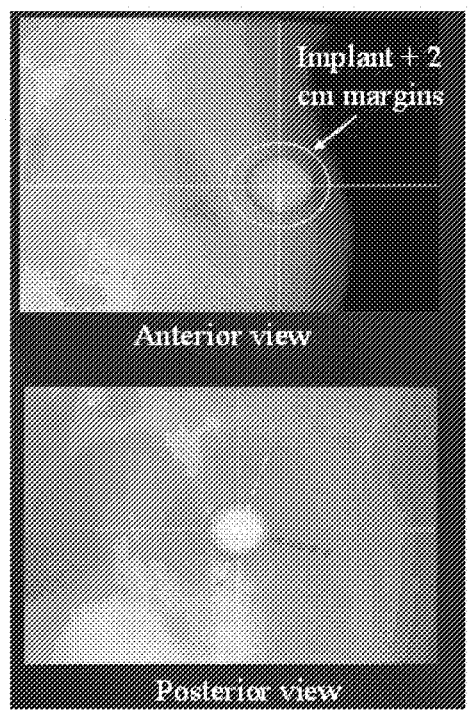
FIG. 6 shows a radiograph with an implanted shaping target device and a treatment margin is shown around the implanted device.
Figure 7:
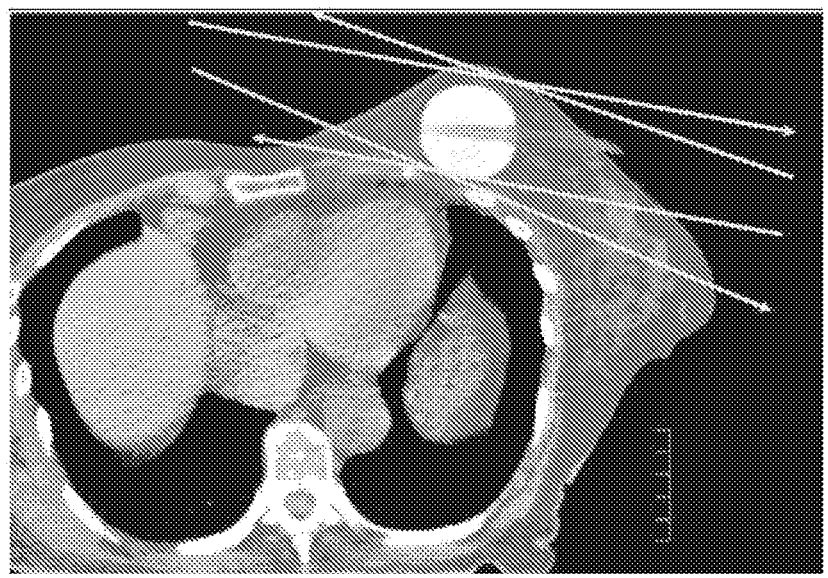
FIG. 7 shows image guided radiotherapy beams intersecting at the implanted device plus margin.

FIGS. 6 and 7 show radiographs of devices of the invention implanted. In FIG. 6, a radiograph shows the implanted shaping target device and a treatment margin is shown around the implanted device. In FIG. 7, image guided radiotherapy beams are shown intersecting at the implanted device and margin of FIG. 6.

Alternatively, the treatment material may be incorporated into the surface of device 10 such that after implantation, the surface elutes the treatment material to surrounding tissue. In yet a further embodiment, the treatment material may be positioned on only part of the implant surface. In further embodiments, where the implant 10 is a bioabsorbable matrix or sponge, the treatment material may be loaded within the matrix and releases as the device is absorbed. Regardless of the method of delivery, the treatment materials may include, by way of non-limiting example, a chemotherapy agent, an anti-neoplastic agent, an anti-angiogenesis agent, an immunomodulator, a hormonal agent, an immunotherapeutic agent, an antibiotic, a radiosensitizing agent, and combinations thereof.

Additional imaging techniques for localizing the implant can include EPIDs (electronic portal imaging devices), linac-mounted x-ray/fluoroscopic imaging systems, KV and MV CT and KV/MV cone beam CT or other non-radiographic localization systems (by way of further example, surgical navigation systems such as those marketed by BrainLab AG, or tracking systems such as those marketed by Calypso Medical Technology).

In addition, further therapeutic energy sources (not just ionizing radiation) may be used for treatment:
- Targeting for treatment with x-rays (MV, KV) and high energy electrons (energy>1 MeV)
- HIFU,
- lithotripsy,
- external microwaves
- directed electromagnetic waves other than ionizing radiation While the specific examples provided relate to treatment of cancer in the breast, the devices and procedures described herein may be used for other anatomic sites, where cosmesis may or may not be necessary.

A person of ordinary skill in the art will appreciate further features and advantages of the invention based on the above-described embodiments. Accordingly, the invention is not to be limited by what has been particularly shown and described, except as indicated by the appended claims or those ultimately provided. All publications and references cited herein are expressly incorporated herein by reference in their entirety, and the invention expressly includes all combinations and sub-combinations of features included above and in the incorporated references.

The invention claimed is:

1. A method for treating a proliferative tissue disease in a patient comprising:
   excising diseased tissue from the patient and thereby creating a tissue cavity;
   placing a bioabsorbable implant within the tissue cavity, the implant having a body that is rigid and has a predetermined size and shape that remains constant prior to implantation, during implantation, and after implantation, the body being configured to exhibit negative contrast under ultrasonic or x-ray visualization;
   determining a location of the implant within the patient using ultrasonic or x-ray imaging apparatuses; and
   treating tissue surrounding the tissue cavity with therapeutic energy sources, wherein the implant remains within the tissue cavity following treatment.

2. The method of claim 1, wherein the implant comprises collagen.

3. The method of claim 1, wherein the treating of tissue with energy sources comprises applying external beam radiation.

4. The method of claim 1, wherein the implant is sized to fill the tissue cavity.

5. The method of claim 1, wherein the implant maintains its predetermined shape for a period of about at least six weeks.

6. The method of claim 1, wherein a diameter of the implant is approximately 2 to 4 centimeters.

7. The method of claim 1, wherein the body comprises a rigid spherical shape including a core and an outer layer, wherein the outer layer is manufactured from a stiffer material as compared to the core.

8. The method of claim 7, wherein the outer layer further comprises one or more of air, gas pockets, or bubbles to facilitate visualization under ultrasound.

9. The method of claim 1, wherein the body comprises a core and an outer layer, wherein the outer layer is manufactured from a stiffer material as compared to the core.

10. The method of claim 9, wherein the outer layer further comprises one or more of air, gas pockets, or bubbles to facilitate visualization under ultrasound.

11. A method for targeting and delivering therapeutic rays to a patient's soft tissue, comprising:
   (a) preparing a treatment plan for a patient, the treatment plan including one or more sessions of radiation treatment;
   (b) imaging an implanted device within soft tissue in the patient, the implanted device comprising a body that is rigid and has a predetermined size and shape that remains constant prior to implantation, during implantation, and after implantation, wherein the implanted device has a density that is lower than a density of the patient's soft tissue, wherein the shape of the body comprises a rigid spherical shape;
   (c) determining a region of target tissue surrounding the implanted device;
   (d) targeting an energy dose from an energy source external to the patient to the region of target tissue; and
   (e) delivering the targeted energy dose, wherein the implanted device remains within the patient's soft tissue following completion of the treatment plan.

12. The method of claim 11, further comprising:
   without removing the implanted device or acting to alter its configuration, repeating, following a passage of time, steps (b) through (e).

13. The method of claim 11, wherein the implanted device has a density of less than or equal to about 1.03 g/cc.

14. The method of claim 11, wherein the implanted device is implanted in a patient's breast.

15. The method of claim 12, wherein the implanted device is bioabsorbable.

16. The method of claim 15, wherein the implanted device remains substantially rigid during the delivery of the targeted energy doses before absorbing.

17. The method of claim 11, further comprising providing fiducial markers in or on the device in order to track the device's position.

18. The method of claim 11, further comprising delivering to the patient a treatment material from the implanted device.

* * * * *